United States Patent
Barr et al.

(10) Patent No.: US 8,024,851 B2
(45) Date of Patent: Sep. 27, 2011

(54) METHOD OF PRODUCING A RADIALLY EXPANDABLE PROSTHESIS

(75) Inventors: Aaron P. Barr, Fishers, IN (US); Michael P. DeBruyne, Bloomington, IN (US); Jay A. Dittman, Indianapolis, IN (US); Micheal C. Hoffa, Brownsburg, IN (US); Jason A. Mead, Plainfield, IN (US); Benjamin Nickless, Gosport, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 912 days.

(21) Appl. No.: 12/021,711

(22) Filed: Jan. 29, 2008

(65) Prior Publication Data

US 2008/0178459 A1    Jul. 31, 2008

Related U.S. Application Data

(60) Provisional application No. 60/897,971, filed on Jan. 29, 2007.

(51) Int. Cl.
     *B23P 13/04*         (2006.01)
(52) U.S. Cl. .......................................................... 29/557
(58) Field of Classification Search ............... 29/557, 29/458, 460; 623/1.36, 1.15, 1.35; 606/153, 606/191, 195, 198
See application file for complete search history.

(56) References Cited

U.S. PATENT DOCUMENTS

| | | | |
|---|---|---|---|
| 4,580,568 A | 4/1986 | Gianturco | 606/198 |
| 5,019,090 A | 5/1991 | Pinchuk | 623/1.15 |
| 5,282,824 A | 2/1994 | Gianturco | 623/1.13 |
| 5,380,304 A | 1/1995 | Parker | 604/526 |
| 5,397,355 A | 3/1995 | Marin et al. | 623/1.2 |
| 5,421,955 A | 6/1995 | Lau et al. | 216/48 |
| 5,562,697 A | 10/1996 | Christiansen | 623/1.16 |
| 5,632,771 A | 5/1997 | Boatman et al. | 623/1.15 |
| 5,700,253 A | 12/1997 | Parker | 604/526 |
| 5,759,192 A | 6/1998 | Saunders | 606/194 |
| 5,780,807 A | 7/1998 | Saunders | 219/121.71 |
| 5,928,280 A | 7/1999 | Hansen et al. | 623/1.15 |
| 5,968,088 A | 10/1999 | Hansen et al. | 623/1.12 |
| 6,042,606 A | 3/2000 | Frantzen | 623/1.18 |
| 6,131,266 A | 10/2000 | Saunders | 29/557 |
| 6,231,598 B1 | 5/2001 | Berry et al. | 623/1.15 |
| 6,254,632 B1 | 7/2001 | Wu et al. | 623/1.15 |
| 6,369,355 B1 | 4/2002 | Saunders | 219/121.71 |
| 6,464,720 B2 | 10/2002 | Boatman et al. | 623/1.15 |
| 6,521,865 B1 | 2/2003 | Jones et al. | 219/121.72 |

(Continued)

FOREIGN PATENT DOCUMENTS

AU      199925127 B2    2/1999

(Continued)

OTHER PUBLICATIONS

International Search Report for corresponding international patent application No. PCT/US2008/001089, dated Jun. 24, 2008.

(Continued)

*Primary Examiner* — John C Hong

(74) *Attorney, Agent, or Firm* — Brinks Hofer Gilson & Lione

(57) ABSTRACT

A method for producing a radially expandable prosthesis by cutting a pattern in a tubular member, which member has an outer diameter at least as great as the expanded diameter of the prosthesis.

20 Claims, 4 Drawing Sheets

U.S. PATENT DOCUMENTS

| | | | |
|---|---|---|---|
| 6,551,341 B2 | 4/2003 | Boylan et al. | 606/200 |
| 6,786,922 B2 | 9/2004 | Schaeffer | 623/1.15 |
| 7,090,694 B1 | 8/2006 | Morris et al. | 623/1.15 |
| 7,914,567 B2 * | 3/2011 | Pavcnik et al. | 623/1.13 |
| 2001/0027339 A1 | 10/2001 | Boatman et al. | 623/1.15 |
| 2002/0002401 A1 | 1/2002 | McGuckin, Jr. et al. | 623/1.19 |
| 2002/0013619 A1 | 1/2002 | Shanley | 623/1.15 |
| 2002/0128707 A1 | 9/2002 | Kavteladze et al. | 623/1.17 |
| 2002/0193866 A1 | 12/2002 | Saunders | 623/1.15 |
| 2003/0036794 A1 | 2/2003 | Ragheb et al. | 623/1.15 |
| 2003/0088310 A1 | 5/2003 | Hansen et al. | 623/1.16 |
| 2003/0105511 A1 | 6/2003 | Welsh et al. | 623/1.15 |
| 2003/0236570 A1 | 12/2003 | Cook et al. | 623/1.36 |
| 2004/0006382 A1 | 1/2004 | Sohier | 623/1.15 |
| 2004/0047909 A1 | 3/2004 | Ragheb et al. | 424/471 |
| 2004/0093071 A1 | 5/2004 | Jang | 623/1.15 |
| 2004/0117004 A1 | 6/2004 | Osborne et al. | 623/1.36 |
| 2004/0148012 A9 | 7/2004 | Jang | 623/1.15 |
| 2004/0204750 A1 | 10/2004 | Dinh | 623/1.15 |
| 2004/0225347 A1 | 11/2004 | Lang | 623/1.15 |
| 2004/0243225 A1 | 12/2004 | Ragheb et al. | 623/1.42 |
| 2004/0249443 A1 | 12/2004 | Shanley et al. | 623/1.15 |
| 2005/0038455 A1 | 2/2005 | Bates et al. | 606/153 |
| 2005/0085898 A1 | 4/2005 | Boatman | 623/1.15 |
| 2005/0113903 A1 | 5/2005 | Rosenthal et al. | 623/1.15 |
| 2005/0131525 A1 | 6/2005 | Hartley | 623/1.15 |
| 2005/0137690 A1 | 6/2005 | Salahieh | 623/2.11 |
| 2005/0159806 A1 | 7/2005 | Shanley | 613/1.15 |
| 2005/0182478 A1 | 8/2005 | Holman et al. | 623/1.15 |
| 2005/0182483 A1 | 8/2005 | Osborne et al. | 623/1.24 |
| 2005/0187604 A1 | 8/2005 | Eells et al. | 623/1.13 |

FOREIGN PATENT DOCUMENTS

| | | |
|---|---|---|
| EP | 1 579 824 A2 | 9/2005 |
| FR | 2 764 794 | 12/1998 |
| WO | WO 97/09945 | 3/1997 |
| WO | WO 00/35378 | 6/2000 |
| WO | WO 2006/099430 A1 | 9/2006 |

OTHER PUBLICATIONS

Written Opinion of the International Searching Authority for corresponding international patent application No. PCT/US2008/001089, dated Jun. 24, 2008.

* cited by examiner

US 8,024,851 B2

METHOD OF PRODUCING A RADIALLY EXPANDABLE PROSTHESIS

RELATED APPLICATIONS

This application claims the benefit of provisional U.S. Patent Application Ser. No. 60/897,971, filed Jan. 29, 2007, which is incorporated herein by reference in its entirety.

TECHNICAL FIELD

The present invention relates generally to medical devices and, in particular, to a method of producing a radially expandable prosthesis.

BACKGROUND

Intraluminal prostheses, such as stents, are generally known. Intraluminal stents may be deployed at a narrowed site in a body lumen, for example a blood vessel, to strengthen, support or repair the lumen. With angioplasty for example, implantations of stents have substantially advanced the treatment of occluded blood vessels. Once implanted, the prosthesis strengthens that part of the vessel such that blood flow is ensured.

Preferably, intraluminal stents have a small cross-sectional diameter and/or profile for introducing the stent into the affected body lumen. A configuration which is extremely suited for implantation in a body lumen is a generally cylindrical prosthesis which can radially expand from a first, small, collapsed diameter to a second, larger, expanded diameter. Such prostheses can be implanted in a body lumen by placing them on a catheter and transporting them through the lumen to the desired location. The prosthesis may be self-expanding or the catheter may be provided with a balloon or another expansion mechanism which exerts a radial outwards pressure on the prosthesis so that the prosthesis expands to a larger diameter.

One method of producing expandable intraluminal prostheses is by cutting a metal cannula around its circumference, for example to form a stent. Typically, the metal cannula is the size of the stent in its collapsed delivery state. Alternatively, the cannula is an intermediate size, between that of the collapsed diameter and expanded diameter of the stent.

Stents formed from an intermediate or collapsed size cannula may undesirably twist during expansion due to the stent's thin bars or struts. Another concern of intermediate or compressed-diameter cannula-formed stents is non-uniform radial expansion of the stent. Thin, flexible strut segments may not deform outwardly in the same manner and to the same degree as strut segments of higher radial strength, possibly resulting in stent segments extending or "hanging" into the lumen. Particularly in vascular stents, local blood flow turbulence can occur at these points that might contribute to thrombus formation. A design that increases longitudinal and radial strength and stability, and evenly distributes bending stresses is less prone to twisting and non-uniform expansion.

Still another consideration is stent migration following implantation due to physiological forces within the body lumen. Pulsatile flow is a major force that stents encounter; thus stents and endoluminal prostheses, if not properly anchored, may move downstream in the blood lumen in which they are placed. If the stents or endoluminal prostheses do migrate, their effectiveness may be diminished. To address migration, manufacturers may solder or otherwise bond outwardly-extending barbs or hooks to the prosthesis. However, non-integral barbs may deform or fracture from repeated physiological stresses, particularly the cyclical loading caused by cardiovascular pulsatile forces.

SUMMARY

A method for producing a radially expandable prosthesis is provided. The method comprises providing a tubular member and cutting the tubular member to form a prosthesis. The prosthesis may be adapted to have a compressed diameter for endoluminal delivery and an expanded diameter for use upon implantation. The tubular member has an outer diameter at least as great as the prosthesis' expanded diameter. Preferably, the tubular member is cut with a laser.

DETAILED DESCRIPTION

Figure 1A:
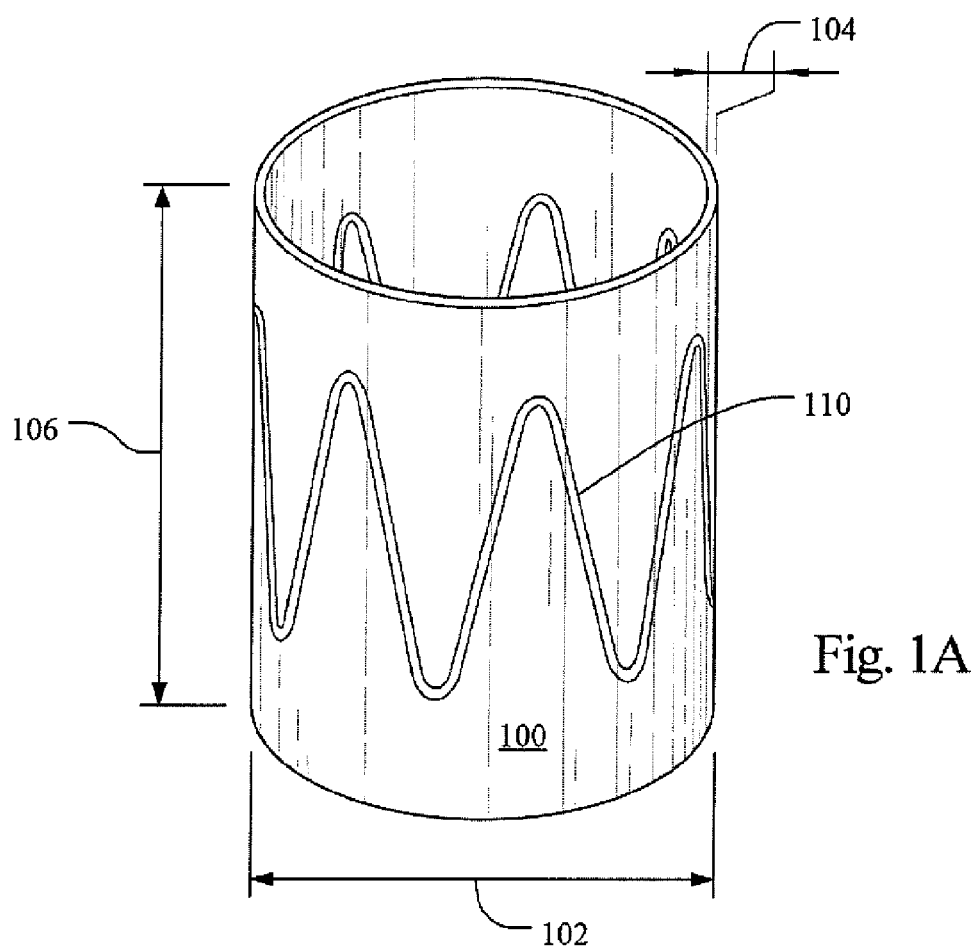
FIG. 1A is a perspective drawing of a tubular member with a zigzag-shaped prosthesis pattern.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "implantable" refers to an ability of a medical device to be positioned at a location within a body, such as within a body lumen.

The term "cavity" as used herein refers to any well, hole, depression, slot, groove, or the like included in the medical device in any manner.

The term "body vessel" means any tube-shaped body passage lumen that conducts fluid, including but not limited to blood vessels such as those of the human vasculature system, esophageal, intestinal, billiary, urethral and ureteral passages.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "endoluminal" describes objects that are found or can be placed inside a lumen or space in the human or animal body. This includes lumens such as blood vessels, parts of the gastrointestinal tract, ducts such as bile ducts, parts of the respiratory system, etc. "Endoluminal prosthesis" thus describes a prosthesis that can be placed inside one of these lumens.

The term "about" used with reference to a quantity includes variations in the recited quantity that are equivalent to the quantity recited, such as an amount that is insubstantially different from a recited quantity for an intended purpose or function.

Typical sites for placement of a prosthesis include the coronary and peripheral vasculature (collectively referred to herein as the vasculature), heart, esophagus, trachea, colon, gastrointestinal tract, biliary tract, urinary tract, bladder, prostate, brain and surgical sites. The prosthesis may be any medical device that is introduced temporarily or permanently into the body for the prophylaxis or therapy of a medical condition. For example, such prostheses may include, but are not limited to, stents, stent grafts, catheters, guidewires, balloons, filters (e.g., vena cava filters), cerebral aneurysm filler coils, intraluminal paving systems, valves (e.g., venous valves), abdominal aortic aneurysm (AAA) grafts, embolic coils, bone substitutes, intraluminal devices, vascular supports, or other known biocompatible devices. Preferably, the prosthesis is a stent.

Intraluminal stents as disclosed here may comprise a patterned tubular member. Examples include endovascular, biliary, tracheal, gastrointestinal, urethral, esophageal and coronary vascular stents. The intraluminal stents may be, for example, balloon-expandable or self-expandable. Thus, although certain examples will be described herein with reference to vascular stents, the present disclosure is applicable to other prostheses, including other types of stents.

The materials used to comprise the prostheses need only be biocompatible or able to be made biocompatible. Examples of suitable materials include, without limitation, stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin, or combinations thereof. Preferably, the prosthesis comprises stainless steel or nitinol.

Methods of Producing Prostheses

In one example, the method comprises providing a tubular member and cutting the tubular member to form a prosthesis. The prosthesis may be balloon-expandable or, preferably, self-expanding and is preferably a stent, for example a bifurcated stent, a stent configured for any blood vessel including coronary arteries and peripheral arteries (e.g., renal, superficial femoral, carotid, and the like), a urethral stent, a biliary stent, a tracheal stent, a gastrointestinal stent, or an esophageal stent. The diameter of the tubular member is at least as large as the expanded diameter of the prosthesis. While a round tubular member and stent are depicted in the examples shown herein, other tubular member shapes, e.g., square, triangular, D-shaped, polygonal, etc., may be used from which a prosthesis may be cut.

The tubular member may be cut in any suitable manner. Preferably, the tubular member is cut using lasers, but may be cut, for example, by sawing, power hacksawing, shearing, abrasive cutting, plasma, or thermal cutting. The prosthesis may have any configuration possible, including but not limited to a sinusoidal shape, a zigzag shape, a mesh of interconnecting struts, or any other suitable configuration. Preferably, the prosthesis has a zigzag shape.

Figure 1B:
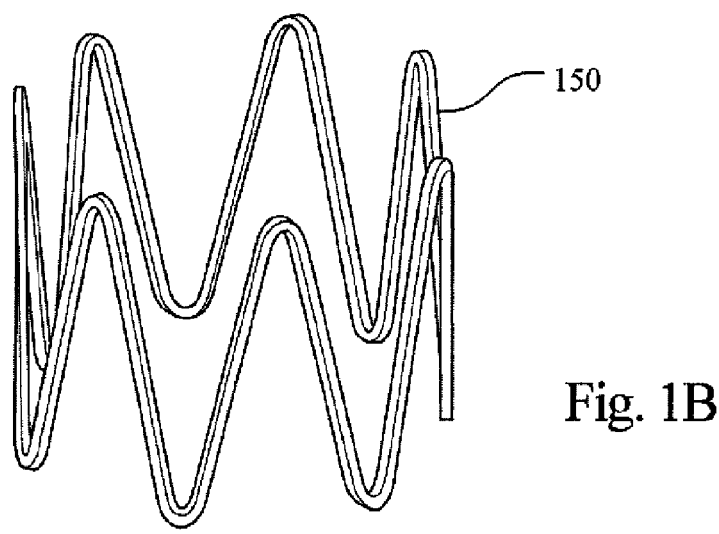
FIG. 1B is a perspective drawing of a zigzag-shaped prosthesis that has been cut from the tubular member of FIG. 1A.

For example, FIG. 1A shows a tubular member 100 from which a prosthesis may be produced. The prosthesis profile 110 shows a pattern with which a prosthesis may be cut. The diameter 102 of the tubular member 100 preferably relates to the desired dimensions of the prosthesis in an expanded state. The wall thickness 104 of the tubular member 100 should approximate the desired thickness of the final prosthesis. The length 106 of the tubular member 100 should accommodate the desired length of the final prosthesis. FIG. 1B illustrates the prosthesis of FIG. 1A after the prosthesis 150 has been cut from the tubular member 100.

Figure 2:
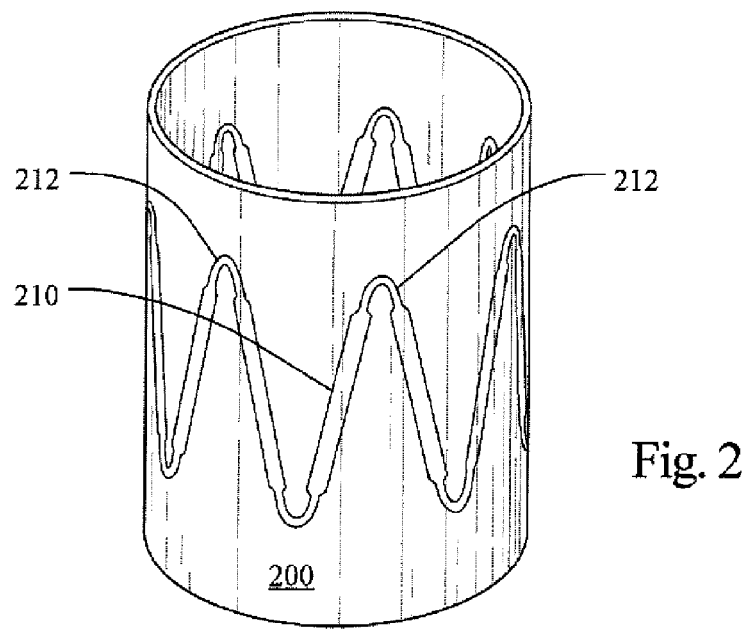
FIG. 2 is a perspective drawing of a tubular member with a zigzag-shaped prosthesis pattern having reduced-width apexes.

In another example, the apexes of a zigzag-shaped prosthesis, for example a stent, may be cut to be thinner than the struts of the prosthesis. For example, FIG. 2 illustrates a tubular member 200 from which a stent may be produced. The stent profile 210 shows a pattern with which a stent comprising reduced diameter apexes 212 may be produced. The result of reduced diameter apexes 212 is that the collapsed configuration of the stent may be much smaller at the ends. By reducing the bulk at the apexes in a collapsed stent, a smaller delivery system may be used.

Structural Features

The prosthesis may optionally include supplemental attachment means, such as anchoring devices, searing, bonding, gluing, or otherwise adhering the prosthesis to the vessel wall or combinations thereof. For example, the prosthesis may be secured in place with one or more anchoring devices.

A wide variety of structural features that are acceptable for use as medical device anchoring devices, and any suitable structural feature can be used. For example, individual barbs may be used to maintain a prosthesis implanted in a body vessel. Anchoring devices may be secured to the prosthesis by any means, including but not limited to welding, stitching, bonding, and adhesives. Preferably, anchoring devices are an integral part of the prosthesis.

Figure 3:
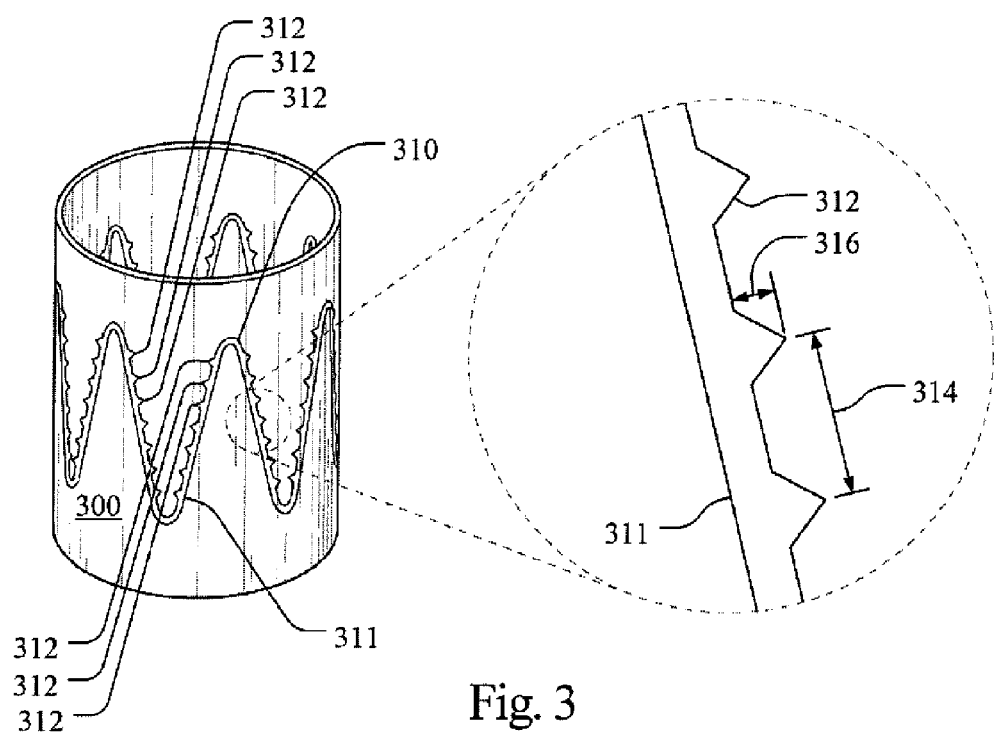
FIG. 3 is a perspective drawing of a tubular member with a zigzag-shaped prosthesis pattern comprising integral barbs.

In one aspect, a prosthesis may comprise features, such as integral barbs, that maintain the prosthesis in position following implantation in a body vessel. Integral barbs eliminate the need for secondary processes and may reduce or eliminate the corrosion potential of a solder or laser-welded joint. For example, FIG. 3 illustrates a prosthesis comprising integral barbs to facilitate maintenance in a body vessel. FIG. 3 depicts a tubular member 300 with line or barb profile 310 from which a prosthesis with integral barbs may be cut. Tubular member 300 has a diameter at least as great as the prosthesis expanded diameter, permitting greater detail and control while laser cutting the barb profile 310.

The number, arrangement, and configuration of integral barbs can vary according to design preference and the clinical use of the prosthesis. For example, the barb profile 310 can be varied. In particular, the distance 314 between barbs 312 and the height 316 and shape of the barbs can be varied. The barbs can have any suitable shape, including points or "fish hook"-like configurations. The opposing side 311 of the prosthesis may also be cut to provide additional barbs. The desired barb profile can be determined by the level of traction that the particular application requires and/or concerns about the damage to the surrounding body vessel that may be caused by the barbs, inter alia.

Figure 4A:
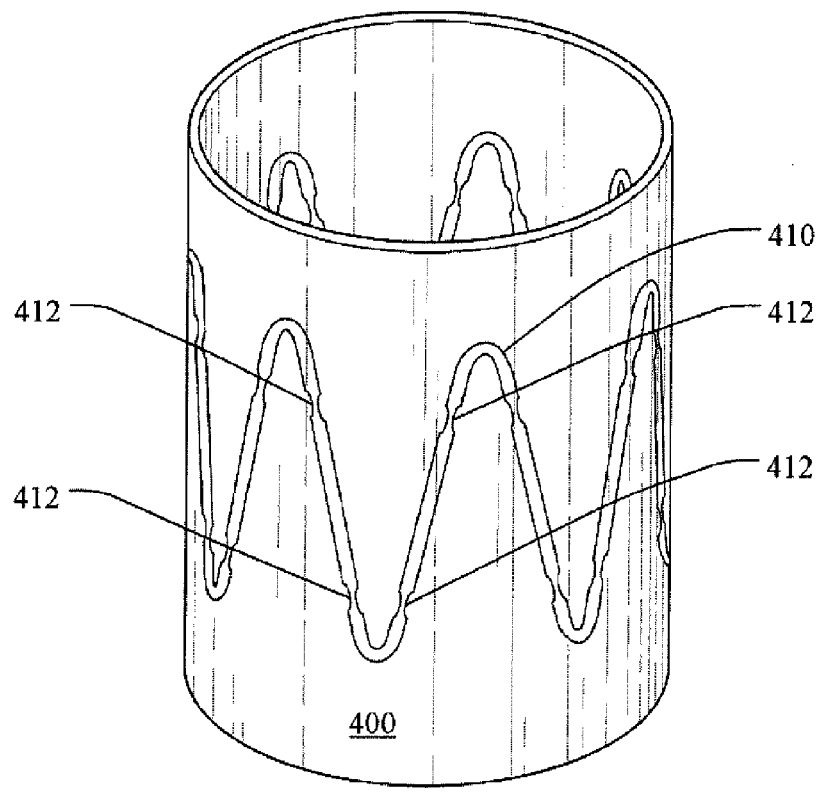
FIG. 4A is a perspective drawing of a tubular member with a zigzag-shaped prosthesis pattern comprising notches.
Figure 4B:
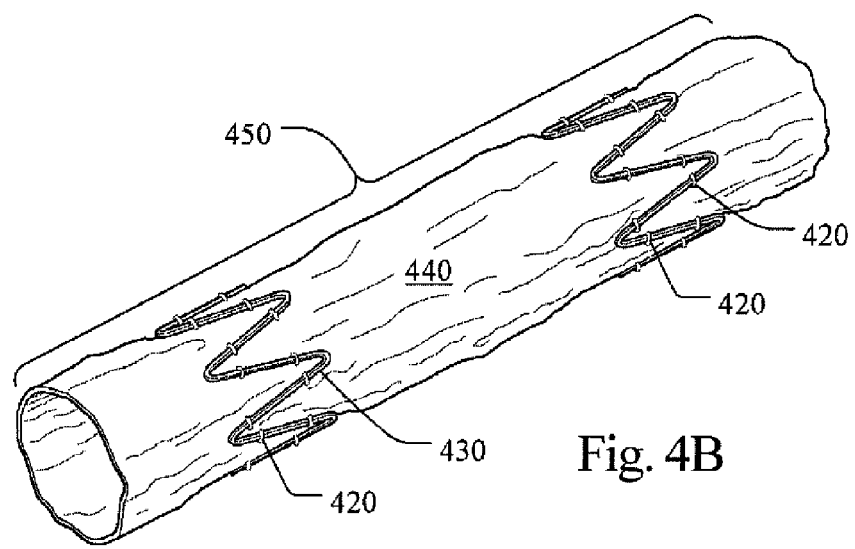
FIG. 4B is a perspective drawing of a zigzag-shaped prosthesis cut from the tubular member of FIG. 4A that is sutured to graft material.

In other examples, the prosthesis may include an area of reduced diameter to aid in operatively connecting a graft material to the device. For example, FIGS. 4A and 4B illustrate a stent with notches 412 to aid in suturing the stent to a graft material. FIG. 4A depicts a tubular member 400 from which a stent may be produced. The line or notch profile 410 shows a pattern with which a stent comprising notches 412 may be cut. Notches 412 are of a reduced width permitting the size of the suture wrap 420 to reduce and permit for a smaller compressed delivery configuration of the stent-graft 450. Additionally, notches 412 permit the medical device to be connected more securely relative to its position on the graft material. This reduces stent 430 to graft 440 wear as the stent 430 moves relative to the graft 440 over extended periods of time. Tubular member 400 has a diameter at least as great as the stent expanded diameter, permitting greater detail and control while laser cutting the notches 412. Alternatively, suture bulk may be reduced with a prosthesis that includes cavities allowing for a continuous suture.

Radiopaque Material

Also provided are examples wherein the prosthesis comprises a means for orienting the prosthesis within a body lumen. For example, a prosthesis may comprise a marker, such as a radiopaque portion of the prosthesis that would be seen by remote imaging methods including X-ray, ultrasound, Magnetic Resonance Imaging and the like, or by detecting a signal from or corresponding to the marker.

Figure 5:
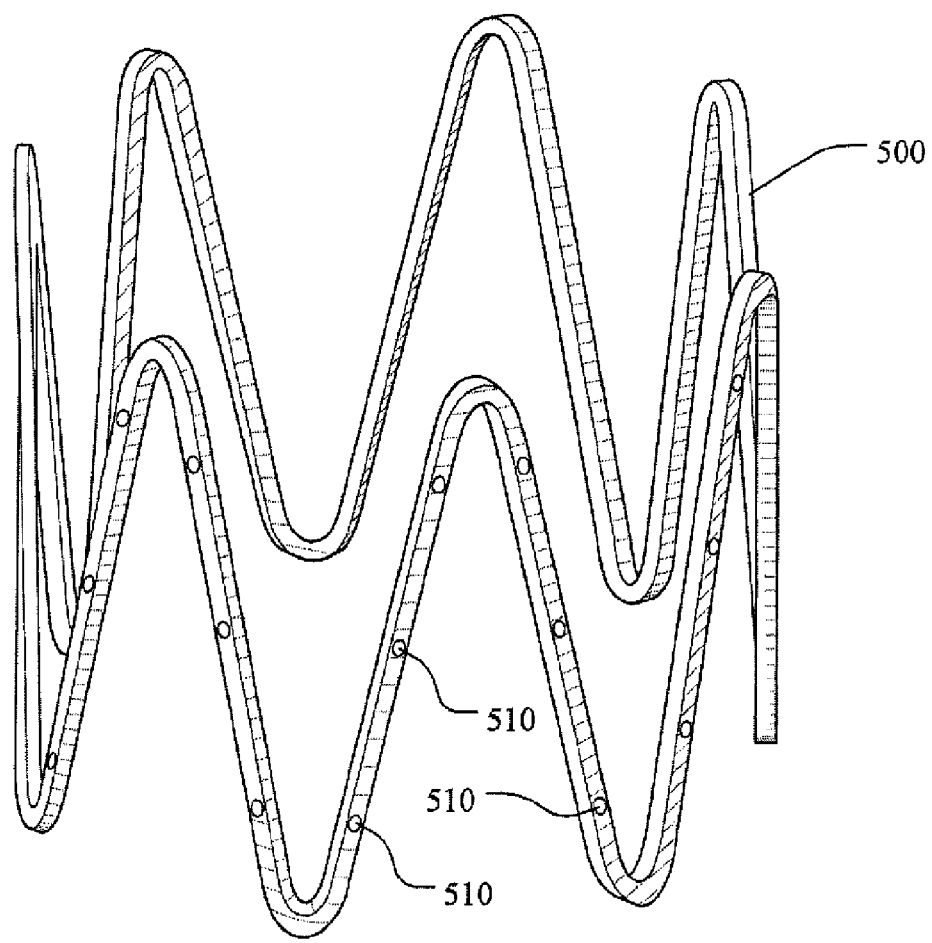
FIG. 5 is a perspective drawing of a prosthesis comprising cavities.

For example, a prosthesis may comprise cavities for receiving a radiopaque material (see, e.g., co-pending U.S. application Ser. No. 10/870,079, incorporated herein by reference). FIG. 5 depicts one example of prosthesis 500 comprising cavities 510 loaded with radiopaque material for orienting the prosthesis 500 within a body lumen. The radiopaque material may be located on the prosthesis in any possible configuration. Preferably, radiopaque material is strategically located on the prosthesis to provide cues for rotational and longitudinal orientation within a body vessel. The degree of radiopacity contrast can be altered by implant content.

In other examples, the delivery device can comprise a frame with radiopaque indicia relating to the orientation of the prosthesis within the body vessel. In other examples, indicia can be located, for example, on a portion of a delivery catheter that can be correlated to the location of the prosthesis within a body vessel.

The prosthesis or delivery device may comprise one or more radiopaque materials to facilitate tracking and positioning of the medical device, which may be added in any fabrication method or absorbed into or sprayed onto the surface of part or all of the prosthesis. Common radiopaque materials include barium sulfate, bismuth subcarbonate, and zirconium dioxide. Other radiopaque elements include: cadmium, tungsten, gold, tantalum, bismuth, platium, iridium, and rhodium. Radiopacity is typically determined by fluoroscope or x-ray film.

Therapeutic Agents

An implantable prosthesis may optionally comprise a bioactive agent. For example, a prosthesis may comprise cavities, similar to those of FIG. 5, that may be loaded with therapeutic agent. Alternatively, prostheses may be coated with therapeutic agent.

Figure 6:
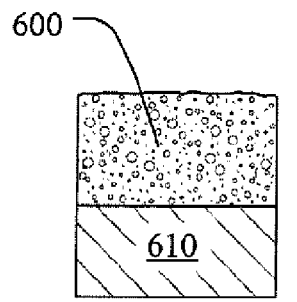
FIG. 6 is a cross-sectional view of a prosthesis coated with therapeutic agent.

For example, a layer of therapeutic agent may be deposited on at least a portion of the surface of a prosthesis, or on a primer layer which is placed directly on the surface of a prosthesis. FIG. 6 shows a cross-sectional view of the surface of a coated prosthesis comprising a first layer of therapeutic agent 600 deposited on a prosthesis 610.

Figure 7:
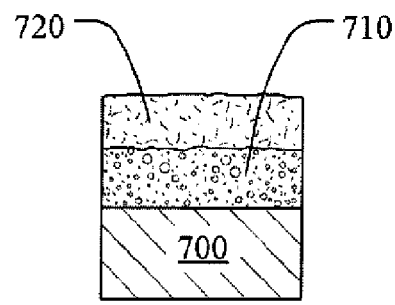
FIG. 7 is a cross-sectional view of a prosthesis coated with therapeutic agent.

The present disclosure also contemplates prostheses having various multiple layer coating configurations. The coating configuration may contain multiple therapeutic agents (hydrophilic and/or hydrophobic), non-polymers (such as a vitamin), a porous biostable polymer, a bioabsorbable polymer, or any combination thereof. For example, FIG. 7 shows a cross-sectional view of the surface of a second coated prosthesis 700 comprising a first layer of therapeutic agent 710 and a second layer of a bioabsorbable polymer 720, such as polylactic acid, to control the rate of therapeutic agent elution.

The coating layer(s) may be deposited on the prosthesis in any suitable manner. For example, the coating may be deposited onto the prosthesis by spraying, dipping, pouring, pumping, brushing, wiping, ultrasonic deposition, vacuum deposition, vapor deposition, plasma deposition, electrostatic deposition, epitaxial growth, or any other method known to those skilled in the art. Prostheses may be coated before or after cutting from a tubular member.

Therapeutic agents that may be used, but are not limited to, pharmaceutically acceptable compositions containing any of the therapeutic agents or classes of therapeutic agents listed herein, as well as any salts and/or pharmaceutically acceptable formulations thereof. Table 1 below provides a non-exclusive list of classes of therapeutic agents and some corresponding exemplary active ingredients.

TABLE 1

| Class | Exemplary Active Ingredients |
| --- | --- |
| Adrenergic agonist | Adrafinil |
|  | Isometheptene |
|  | Ephedrine (all forms) |
| Adrenergic antagonist | Monatepil maleate |
|  | Naftopidil |
|  | Carvedilol |
|  | Moxisylyte HCl |
| Adrenergic - Vasoconstrictor/Nasal decongestant | Oxymetazoline HCl |
|  | Norfenefrine HCl |
|  | Bretylium Tosylate |
| Adrenocorticotropic hormone | Corticotropin |
| Analgesic | Bezitramide |
|  | Bupivacaine |
|  | Acetylsalicysalicylic acid |
|  | Propanidid |
|  | Lidocaine |
|  | Pseudophedrine hydrochloride |
|  | Acetominophen |
|  | Chlorpheniramine Maleate |
| Anesthetics | Dyclonine HCl |

TABLE 1-continued

| Class | Exemplary Active Ingredients |
|---|---|
| Anthelmintics | Hydroxydione Sodium<br>Acetamidoeugenol<br>Niclosamide<br>Thymyl N-Isoamylcarbamate<br>Oxamniquine<br>Nitroxynil N-ethylglucamine<br>Anthiolimine |
| Anti-inflammatory | 8-Hydroxyquinoline Sulfate<br>Bendazac<br>Bufexamac<br>Desoximetasone<br>Amiprilose HCl<br>Balsalazide Disodium Salt<br>Benzydamine HCl |
| Antiallergic | Fluticasone propionate<br>Pemirolast Potassium salt<br>Cromolyn Disodium salt<br>Nedocromil Disodium salt |
| Antiamebic | Cephaeline<br>Phanquinone<br>Thiocarbarsone |
| Antianemic | Folarin<br>Calcium folinate |
| Antianginal | Verapamil<br>Molsidomine<br>Isosorbide Dinitrate<br>Acebutolol HCl<br>Bufetolol HCl<br>Timolol Hydrogen maleate salt |
| Antiarrhythmics | Quinidine<br>Lidocaine<br>Capobenic Acid<br>Encainide HCl<br>Bretylium Tosylate<br>Butobendine Dichloride |
| Antiarthritics | Azathioprine<br>Calcium 3-aurothio-2-propanol-1-sulfate<br>Glucosamine Beta Form<br>Actarit |
| Antiasthmatics/Leukotriene antagonist | Cromalyn Disodium<br>Halamid<br>Montelukast Monosodium salt |
| Antibacterial | Cefoxitin Sodium salt<br>Lincolcina<br>Colisitin sulfate |
| Antibiotics | Gentamicin<br>Erythromycin<br>Azithromycin |
| Anticoagulants | Heparin sodium salt<br>Dextran Sulfate Sodium |
| Anticonvulsants | Paramethadione<br>Phenobarbital sodium salt<br>Levetiracetam |
| Antidepressants | Fluoxetine HCl<br>Paroxetine<br>Nortiptyline HCl |
| Antidiabetic | Acarbose<br>Novorapid<br>Diabex |
| Antiemetics | Chlorpromazine HCl<br>Cyclizine HCl<br>Dimenhydrinate |
| Antiglaucoma agents | Dorzolamide HCl<br>Epinepherine (all forms)<br>Dipivefrin HCl |
| Antihistamines | Histapyrrodine HCl |
| Antihyperlipoproteinemic | Lovastatin<br>Pantethine |
| Antihypertensives | Atenolol<br>Guanabenz Monoacetate<br>Hydroflumethiazide |
| Antihyperthyroid | Propylthiouracil<br>Iodine |
| Antihypotensive | Cartonsor<br>Pholedrine Sulfate<br>Norepinephrine HCl |
| Antimalarials | Cinchonidine<br>Cinchonine<br>Pyrimethamine<br>Amodiaquin Dihydrochloride dihydrate<br>Bebeerine HCl<br>Chloroquine Diphosphate |
| Antimigraine agents | Dihydroergotamine<br>Ergotamine<br>Eletriptan Hydrobromide<br>Valproic Acid Sodium salt<br>Dihydroergotamine mesylate |
| Antineoplastic | 9-Aminocamptothecin<br>Carboquone<br>Benzodepa<br>Bleomycins<br>Capecitabine<br>Doxorubicin HCl |
| Antiparkinsons agents | Mothixene<br>Terguride<br>Amantadine HCl<br>Ethylbenzhydramine HCl<br>Scopolamine N-Oxide Hydrobromide |
| Antiperistaltic; antidiarrheal | Bismuth Subcarbonate<br>Bismuth Subsalicylate<br>Mebiquine<br>Diphenoxylate HCl |
| Antiprotozoal | Fumagillin<br>Melarsoprol<br>Nitazoxanide<br>Aeropent<br>Pentamideine Isethionate<br>Oxophenarsine Hydrochloride |
| Antipsycotics | Chlorprothixene<br>Cyamemazine<br>Thioridazine<br>Haloperidol HCl<br>Triflupromazine HCl<br>Trifluperidol HCl |
| Antipyretics | Dipyrocetyl<br>Naproxen<br>Tetrandrine<br>Imidazole Salicylate<br>Lysine Acetylsalicylate<br>Magnesium Acetylsalicylate |
| Antirheumatic | Auranofin<br>Azathioprine<br>Myoral<br>Penicillamine HCl<br>Chloroquine Diphosphate<br>Hydroxychloroquine Sulfate |
| Antispasmodic | Ethaverine<br>Octaverine<br>Rociverine<br>Ethaverine HCl<br>Fenpiverinium Bromide<br>Leiopyrrole HCl |
| Antithrombotic | Plafibride<br>Triflusal<br>Sulfinpyrazone<br>Ticlopidine HCl |
| Antitussives | Anethole<br>Hydrocodone<br>Oxeladin<br>Amicihone HCI<br>Butethamate Citrate<br>Carbetapentane Citrate |
| Antiulcer agents | Polaprezinc<br>Lafutidine<br>Plaunotol<br>Ranitidine HCl<br>Pirenzepine 2 HCl<br>Misoprostol |
| Antiviral agents | Nelfinavir<br>Atazanavir<br>Amantadine<br>Acyclovir<br>Rimantadine HCl |

TABLE 1-continued

| Class | Exemplary Active Ingredients |
|---|---|
| Anxiolytics | Epivar |
|  | Crixivan |
|  | Alprazolam |
|  | Cloxazolam |
|  | Oxazolam |
|  | Flesinoxan HCl |
|  | Chlordiazepoxide HCl |
|  | Clorazepic Acid Dipotassium salt |
| Bronchodialtor | Epinephrine |
|  | Theobromine |
|  | Dypylline |
|  | Eprozinol 2HCl |
|  | Etafedrine |
| Cardiotonics | Cymarin |
|  | Oleandrin |
|  | Docarpamine |
|  | Digitalin |
|  | Dopamine HCl |
|  | Heptaminol HCl |
| Cholinergic | Eseridine |
|  | Physostigmine |
|  | Methacholine Chloride |
|  | Edrophonium chloride |
|  | Juvastigmin |
| Cholinergic antagonist | Pehencarbamide HCl |
|  | Glycopyrrolate |
|  | Hyoscyamine Sulfate dihydrate |
| Cognition enhancers/Nootropic | Idebenone |
|  | Tacrine HCl |
|  | Aceglutamide Aluminum Complex |
|  | Acetylcarnitine L HCl |
| Diagnostic aid | Disofenin |
|  | Ethiodized Oil |
|  | Fluorescein |
|  | Diatrizoate sodium |
|  | Meglumine Diatrizoate |
| Diuretics | Bendroflumethiazide |
|  | Fenquizone |
|  | Mercurous Chloride |
|  | Amiloride HCl2H$_2$O |
|  | Manicol |
|  | Urea |
| Enzyme inhibitor (proteinase) | Gabexate Methanesulfonate |
| Fungicides | Candicidin |
|  | Filipin |
|  | Lucensomycin |
|  | Amphotericin B |
|  | Caspofungin Acetate |
|  | Viridin |
| Gonad stimulating principle | Clomiphene Citrate |
|  | Chorionic gonadotropin |
|  | Humegon |
|  | Luteinizing hormone (LH) |
| Hemorrheologic agent | Poloxamer 331 |
|  | Azupentat |
| Hemostatic | Hydrastine |
|  | Alginic Acid |
|  | Batroxobin |
|  | 6-Aminohexanoic acid |
|  | Factor IX |
|  | Carbazochrome Salicylate |
| Hypolimpernic agents | Clofibric Acid Magnesium salt |
|  | Dextran Sulfate Sodium |
|  | Meglutol |
| Immunosuppresants | Azathioprine |
|  | 6-Mercaptopurine |
|  | Prograf |
|  | Brequinar Sodium salt |
|  | Gusperimus Trihydrochloride |
|  | Mizoribine |
|  | Rapamycin and analogs thereof |
| Mydriatic; antispasmodic | Epinephrine |
|  | Yohimbine |
|  | Aminopentamide dl-Form |
|  | Atropine Methylnitrate |
|  | Atropine Sulfatemonohydrate |
|  | Hydroxyamphetamine (I, HCl, HBr) |
| Neuromuscular blocking agent/ Muscle relaxants (skeletal) | Phenprobamate |
|  | Chlorzoxazone |
|  | Mephenoxalone |
|  | Mioblock |
|  | Doxacurium Chloride |
|  | Pancuronium bromide |
| Oxotocic | Ergonovine Tartrate hydrate |
|  | Methylergonovine |
|  | Prostaglandin F$_{2\alpha}$ |
|  | Intertocine-S |
|  | Ergonovine Maleate |
|  | Prostoglandin F$_{2\alpha}$ Tromethamine salt |
| Radioprotective agent | Amifostine 3H$_2$O |
| Sedative/Hypnotic | Haloxazolam |
|  | Butalbital |
|  | Butethal |
|  | Pentaerythritol Chloral |
|  | Diethylbromoacetamide |
|  | Barbital Sodium salt |
| Serenic | Eltoprazine |
| Tocolytic agents | Albuterol Sulfate |
|  | Terbutaline sulfate |
| Treatment of cystic fibrosis | Uridine 5'-Triphosphate Trisodium dihydrate salt |
| Vasoconstrictor | Nordefrin (−) Form |
|  | Propylhexedrine dl-form |
|  | Nordefrin HCl |
| Vasodilators | Nylidrin HCl |
|  | Papaverine |
|  | Erythrityl Tetranitrate |
|  | Pentoxifylline |
|  | Diazenium diolates |
|  | Citicoline |
|  | Hexestrol |
|  | Bis(diethylaminoethyl ether) 2HCl |
| Vitamins | α-Carotene |
|  | β-Carotene |
|  | Vitamin D$_3$ |
|  | Pantothenic Acid sodium salt |

Other desirable therapeutic agents include, but are not limited to, the following: (a) anti-inflammatory/immunomodulators such as dexamethasone, m-prednisolone, interferon g-1b, leflunomide, sirolimus, tacrolimus, everolimus, pimecrolimus, biolimus (such as Biolimus A7 or A9) mycophenolic acid, mizoribine, cyclosporine, tranilast, and viral proteins; (b) antiproliferatives such as paclitaxel or other taxane derivatives (such as QP-2), actinomycin, methothrexate, angiopeptin, vincristine, mitomycine, statins, C MYC antisense, ABT-578, RestenASE, Resten-NG, 2-chloro-deoxyadenosine, and PCNA ribozyme; (c) migration inhibitors/ECM-modulators such as batimastat, prolyl hydroxylase inhibitors, halofuginone, C proteinase inhibitors, and probucol; and (d) agents that promote healing and re-endotheliazation such as BCP671, VEGF, estradiols (such as 17-beta estradiol (estrogen)), NO donors, EPC antibodies, biorest, ECs, CD-34 antibodies, and advanced coatings.

Any single therapeutic agent or combination of therapeutic agents may be used in the prosthesis. In one example, the therapeutic agent is paclitaxel or a derivative thereof. Paclitaxel may be used to prevent restenosis by preventing chronic inflammation (by preventing the division of affected cells by stabilizing the microtubule function) and by preventing cell migration (by preventing the cell with destructive potential from migrating and accumulating at the injured site).

One or more primer layers, or adhesion promotion layers, may be used with the prosthesis. Such layers may include, for example, silane, acrylate polymer/copolymer, acrylate carboxyl and/or hydroxyl copolymer, polyvinylpyrrolidone/vinylacetate copolymer, olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones.

Finishing

Following the cutting process, the prosthesis may be rough in areas or have sharp or jagged edges, or other surface defects. Mechanical and/or chemical stress may tend to concentrate around those surface defects. Therefore, prostheses properties can often be improved when such surface defects are removed. Surface defects are preferably removed by polishing the prosthesis. Polishing, as used herein, may refer to any type of polishing including, but not limited to, electropolishing, mechanical polishing, chemical polishing, slurry polishing, as well as filing, tumbling in fine media buffing, grinding, or any other suitable method. In one example, polishing of the prosthesis includes electro-polishing.

Electro-polishing is the electrolytic removal of a metal in a preferably highly ionic solution by means of electrical potential and current. Electro-polishing may be used to smooth, polish, de-burr or clean an electrically conductive material. It may remove stress concentrations by selectively removing surface defects on metal surfaces, thereby making the material stronger. Electro-polishing can also improve corrosion resistance and remove hydrogen from the surface of the stent.

The electro-polishing process preferably begins with the preparation of the prosthesis by cleaning it, which can remove non-conductive material from the prosthesis surface. Oils, glues and other substances are possible contaminants. Then, the prosthesis may be electro-polished by placing it in an acid bath, preferably a phosphoric and sulfuric acid solution, and connecting the positive lead of a DC power supply to the prosthesis and a negative lead to a cathode. Post-treatment preferably involves placing the prosthesis in a nitric acid rinse followed by a water rinse.

Delivery of Prostheses

The prostheses are preferably configured for endoluminal delivery to a body vessel. For example, a prosthesis is compressed to a delivery configuration within a retaining sheath that is part of a delivery system, such as a catheter-based system. Upon delivery, the prosthesis can be expanded, for example, by inflating a balloon from inside the prosthesis. The delivery configuration can be maintained prior to deployment of the prosthesis by any suitable means, including a sheath, a suture, a tube or other restraining material around all or part of the compressed prosthesis, or other methods.

Prostheses can be deployed in a body lumen by any means appropriate to their design. The prostheses may be adapted for deployment using conventional methods known in the art and employing percutaneous transluminal catheter devices. The prostheses are designed for deployment by any of a variety of in situ expansion means.

In one example, the prostheses is a self-expanding stent. In this example, the stent is mounted onto a catheter that holds the prosthesis as it is delivered through the body vessel and then releases the prosthesis and allows it to self-expand into contact with the body vessel walls. This deployment is effected after the stent has been introduced percutaneously, transported transluminally and positioned at a desired location by means of the catheter. The self-expanding stent may be deployed according to well-known deployment techniques for self-expanding medical devices. For example, the stent may be positioned at the distal end of a catheter with a removable sheath or sleeve placed over the stent to hold the stent in a contracted state with a relatively small diameter. The prosthesis may then be implanted at the point of treatment by advancing the catheter over a guidewire to the location of the treatment and then withdrawing the sleeve from over the prosthesis. The stent will automatically expand and exert pressure on the wall of the blood vessel at the site of treatment. The catheter, sleeve, and guidewire may then be removed from the patient.

In some examples, a bioabsorbable suture or sheath can be used to maintain a self-expanding prosthesis in a compressed configuration both prior to and after deployment. As the bioabsorbable sheath or suture is degraded by the body after deployment, the prosthesis can expand within the body vessel. In some examples, a portion of the prosthesis can be restrained with a bioabsorbable material and another portion allowed to expand immediately upon implantation.

In another example, the prosthesis is first positioned to surround a portion of an inflatable balloon catheter. The prosthesis, with the balloon catheter inside is configured at a first, collapsed diameter. The device and the inflatable balloon are percutaneously introduced into a body vessel, following a previously positioned guidewire. The prosthesis may be tracked by a fluoroscope, until the balloon portion and associated device are positioned within the body vessel at the point where the prosthesis is to be placed. Thereafter, the balloon is inflated and the prosthesis is expanded by the balloon portion from the collapsed diameter to a second expanded diameter. After the prosthesis has been expanded to the desired final expanded diameter, the balloon is deflated and the catheter is withdrawn, leaving the prosthesis in place. The prosthesis may be covered by a removable sheath during delivery to protect both the prosthesis and the vessels.

Throughout this specification various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

The invention claimed is:

1. A method of producing a radially expandable prosthesis, comprising:
providing a tubular member having an outer diameter;
cutting a pattern in the tubular member to provide a tubular prosthesis where the tubular prosthesis is adapted to have a compressed diameter for endoluminal delivery and an expanded diameter for use upon implantation;
where the tubular member outer diameter is at least as great as the prosthesis expanded diameter.

2. The method of claim 1, where the pattern comprises anchoring members.

3. The method of claim 2, where the anchoring members comprise integral barbs.

4. The method of claim 1, where the pattern comprises notches.

5. The method of claim 1, further comprising forming at least one cavity in the prosthesis.

6. The method of claim 5, where the at least one cavity is at least partially loaded with a therapeutic agent.

7. The method of claim 5, where the at least one cavity is at least partially loaded with a radiopaque material.

8. The method of claim 1, further comprising finishing the prosthesis.

9. The method of claim 8, where the finishing comprises electro-polishing the prosthesis.

10. The method of claim 1, further comprising coating the prosthesis with a therapeutic agent.

11. The method of claim 10, where the therapeutic agent is selected from the group consisting of anti-inflammatory/immunomodulators, antiproliferatives, migration inhibitors/ECM-modulators, and agents that promote healing.

12. The method of claim 11, where the therapeutic agent comprises paclitaxel or a paclitaxel derivative.

13. The method of claim 1, where the tubular member comprises material selected from the group consisting of stainless steel, nitinol, tantalum, a nonmagnetic nickel-cobalt-chromium-molybdenum alloy, platinum, titanium, a suitable biocompatible alloy, a suitable biocompatible material, and a combination thereof.

14. The method of claim 13, where the tubular member material comprises nitinol or stainless steel.

15. A method of producing a radially expandable prosthesis, comprising:
providing a tubular member having an outer diameter;
laser cutting a continuous pattern in the tubular member to provide a tubular prosthesis where the tubular prosthesis is adapted to have a compressed diameter for endoluminal delivery and an expanded diameter for use upon implantation;
where the tubular member outer diameter is at least as great as the prosthesis expanded diameter.

16. The method of claim 15, where the continuous pattern comprises a zigzag shape.

17. The method of claim 16, where the zigzag shape comprises apexes and struts, the apexes comprising a smaller width than the struts.

18. The method of claim 16, where the continuous pattern further comprises integral barbs.

19. The method of claim 16, where the continuous pattern further comprises notches.

20. A method of producing a radially expandable stent, comprising:
providing a tubular member having an outer diameter;
laser cutting a zigzag pattern to provide a zigzag stent comprising apexes and struts;
where the zigzag stent is adapted to have a compressed diameter for endoluminal delivery and an expanded diameter for use upon implantation;
where the apexes have a width less than the struts;
where the struts comprise integral barbs;
where the tubular member outer diameter is at least as great as the expanded diameter of the stent.

* * * * *